United States Patent [19]
Kaufmann et al.

[11] Patent Number: 5,263,978
[45] Date of Patent: Nov. 23, 1993

[54] BLOOD PUMP FOR PULSATING OPERATION

[75] Inventors: Ralf Kaufmann, Aachen; Helmut Reul, Dueren; Guenter Rau, Aachen, all of Fed. Rep. of Germany; Ralf Bitdinger, Grenoble, France

[73] Assignee: Forschungsgesellschaft für Biomedizinische Technik e.V., Aachen, Fed. Rep. of Germany

[21] Appl. No.: 947,757

[22] Filed: Sep. 9, 1992

[30] Foreign Application Priority Data

Sep. 10, 1991 [DE] Fed. Rep. of Germany ....... 4129970

[51] Int. Cl.⁵ .............................................. A61M 1/12
[52] U.S. Cl. ...................................... 623/3; 417/415; 417/419
[58] Field of Search ............................ 600/16–17; 623/3; 417/413, 415, 419

[56] References Cited

U.S. PATENT DOCUMENTS

| | | | |
|---|---|---|---|
| 2,810,347 | 10/1957 | Rippingille | 623/3 X |
| 4,296,500 | 10/1981 | Monties et al. | 623/3 |
| 4,623,350 | 11/1986 | Lapeyre et al. | 623/3 |
| 4,718,903 | 1/1988 | Min et al. | 623/3 |
| 5,006,104 | 4/1991 | Smith et al. | 600/16 |

FOREIGN PATENT DOCUMENTS

| | | | |
|---|---|---|---|
| 0146445 | 11/1984 | European Pat. Off. | |
| 1192787 | 5/1965 | Fed. Rep. of Germany | 623/3 |
| 3136969 | 4/1983 | Fed. Rep. of Germany | 623/3 |
| 3317156 | 5/1983 | Fed. Rep. of Germany | |

OTHER PUBLICATIONS

D. K. Backman et al., Trans. Amer. Soc. Int. Organs, 19 [1973], p. 547–"The Design and Evaluation of Ventricles . . . Power Source".

S. Takatani et al. IEEE 9th Annual Conference of the Engineering & Medical & Biological Society 1987–Development of a Motor-Driven . . . Heart.

Biomed. Technik 35 [1990] pp. 290–301–Preliminary Experience With a New Blood Pump.

*Primary Examiner*—David Isabella
*Assistant Examiner*—D. Willse
*Attorney, Agent, or Firm*—Diller, Ramik & Wight

[57] ABSTRACT

A blood pump housing (43) accommodates at least one piston (21a,21b) driven by a coupling point (19a,19b) on a triangular closed hypocycloidal path ($Z_a$, $Z_b$). The piston (21a,21b) is provided for periodically pressing and releasing a blood chamber (37a,37b). One of the corners of the triangular closed hypocycloidal path ($Z_a,Z_b$) is directed towards the piston (21a,21b), so that the piston movements substantially consist of three periods, i.e. an advance stroke period, a return stroke period and a stationary stroke period.

16 Claims, 6 Drawing Sheets

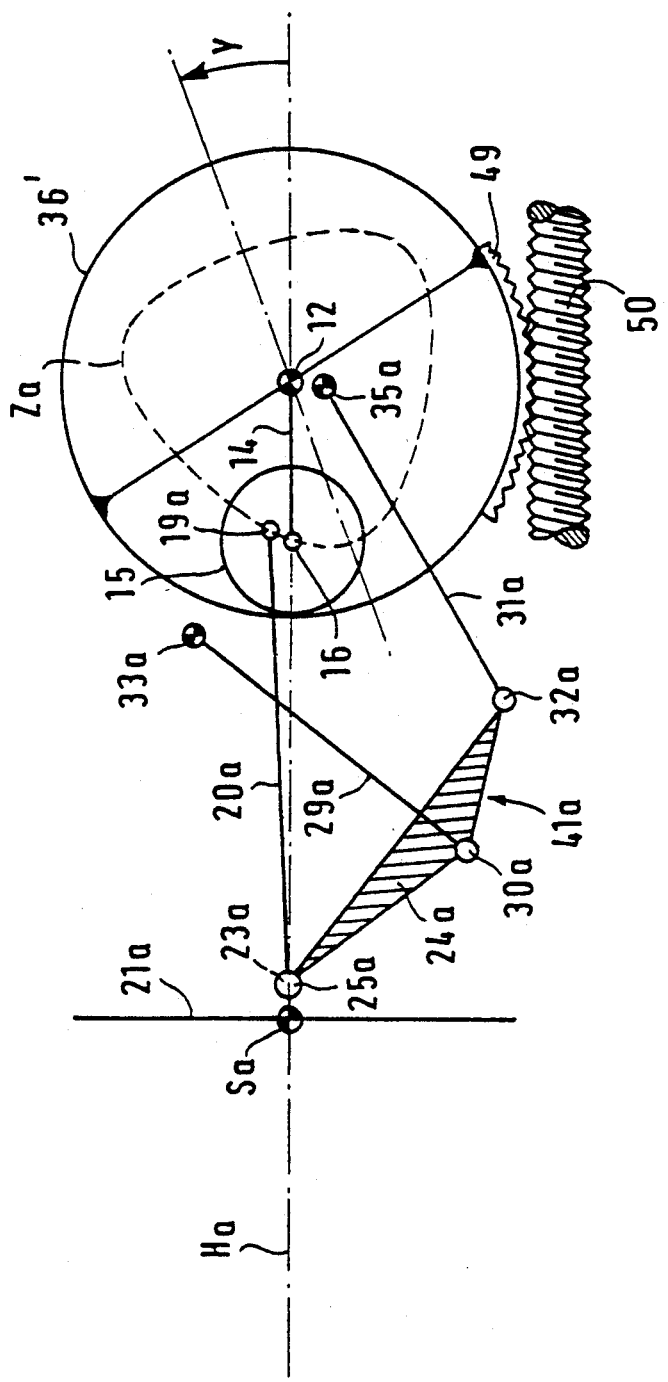

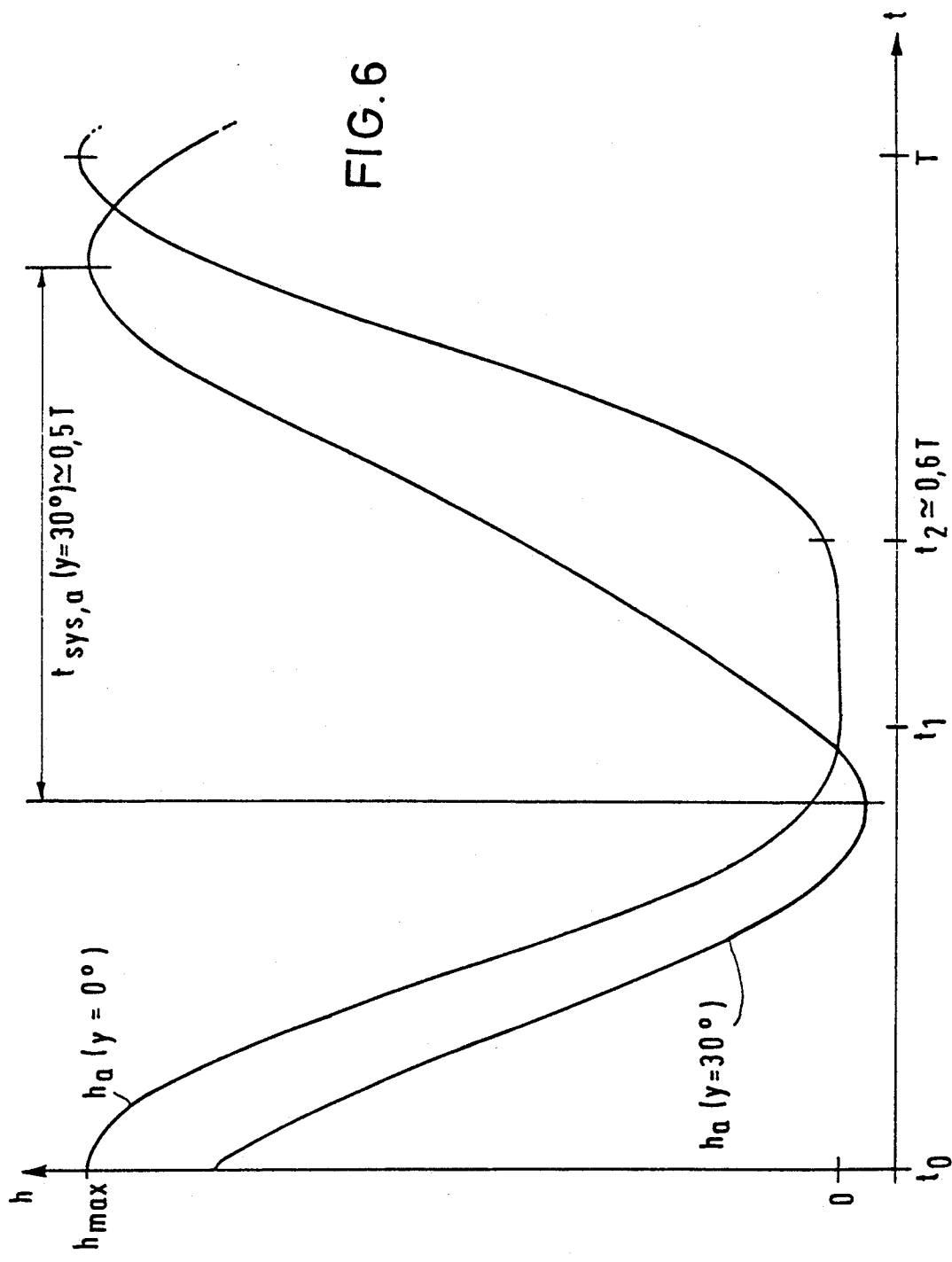

BLOOD PUMP FOR PULSATING OPERATION

The invention is directed to a blood pump.

Blood pumps for pulsating operation are widely used as an artificial heart substitute or as a supporting pump for the human heart. Blood pumps which are used as a heart substitute, i.e. as an implant, must be built extremely wear-resistant and have the highest possible efficiency because they are battery-powered and corrections in the apparatus or the power supply system are possible only in a surgical procedure. Further, a blood pump of this type should perform the pumping movement in a manner similar to the pumping characteristic of the natural heart.

In a known blood pump, the pumping movement is generated by a crank gear (D.K. Backman et al., Trans. Amer. Soc. Int. Organs, 19 542-7 [1973], p. 547). In this known pump, two opposite chambers are alternatively changed in volume by pistons arranged in abutment with membranes. A double piston is driven by said crank gear for carrying out linear strokes. Such a drive means requires a sliding guidance of the crank bearings and thus is susceptible to wear. In addition, the efficiency of the drive means is low since only one geometrical component of the force is made use of for the driving, while a counterfriction has to be overcome at the same time. Due to the continuous operation of the motor, the time periods for the strokes and the return strokes have equal length. Further, there is known a double-acting cam-drum gear pump (S. Takatani et al., IEEE 9th Annual Conference of the Engineering and Medicinal and Biological Society, 1987). In this pump, two opposite pistons are synchronously moved apart from each other and back towards each other. The movement of the piston is effected by two drums acting in opposite senses and being in mutual engagement. The two drums are moved by a cam arranged on a motor shaft. The movement of the motor is reversible for allowing the drums to be moved away from each other and back towards each other. This results in low efficiency while causing increased wear. Also in this apparatus, the time periods for the strokes and the return strokes are equal.

A blood pump known from DE-C-33 17 156 comprises a three-legged piston and operates according to the principle of a pump with a rotational piston. The interior of the rotational piston accommodates the drive unit consisting of an electric motor and a planetary gearing. The piston is moved in a housing having a trochoidal path formed in its casing and comprising suction and discharge openings. This blood pump has high power consumption because the piston with its relatively large mass has to be moved along the out-of-round path of the casing. Further, the systole and the diastole have equal length so that an unphysiological suction underpressure has to be precluded by enlarged suction openings. The blood pump known from EP-B-0 146 445, again provided for pulsating operation, comprises at least one chamber located in a pump housing and an operating device driven by a rotating motor and having a gear unit for moving a coupling point along a circular path, the coupling point driving a piston to periodically change the volume of the chamber. For physiologically imitating the relation between the systole and the diastole, this blood pump requires permanent variation of the number of rotations of the motor in dependence of the blood pressure detected by a sensor.

SUMMARY OF THE INVENTION

It is an object of the invention to provide a blood pump designed for pulsating operation, which imitates the development in time of the pressure changes of the natural heart by use of simple means while the number of rotations of the motor is kept constant.

The blood pump of the invention, due to the control of the piston through a closed hypocycloidal path, has asymmetric pump characteristics corresponding to the physiological division into a blood exhaust period (systole) and a subsequent chamber filling period (diastole), with the pumping effect being intermittent and followed by a relatively long filling period. Each of the pistons successively follows an advance stroke period, a return stroke period and a stationary stroke period without spasmodic movements. While carrying out this cycle, the rotational speed of the motor is kept constant. The asymmetrical pumping characteristics are obtained by a simple arrangement allowing a compact construction of the blood pump with a low weight.

The advance stroke period, which corresponds to the systole, is shorter than half the overall length of the three stroke periods. The division of the diastole into the return stroke period and the stationary stroke period makes it possible to obtain pumping characteristics adapted to the natural heart since the return movement of the piston is faster than the filling speed of the chamber. The filling of the chamber starts during the relatively fast return stroke movement of the piston and is continued in the stationary stroke period. The filling process occurs exclusively through the venous system in dependence of the blood pressure of the patient provided with the blood pump. Since the piston is not fixedly connected to the chamber, the return stroke period will generate no underpressure involving an undesired suction effect in the chamber. During the stationary stroke period, the chamber is filled to its full capacity. Therefore, it is important that the piston does not perform larger stroke movements in the stationary stroke period. To this purpose, it is suitable to use a convex (spherical) hypocycloidal path wherein the edges are rounded.

The motor can be e.g. a speed-controlled DC motor or a piezoelectric motor. By means of sensors, arranged e.g. in or on one of the chambers and detecting the filling condition or the filling speed of the chamber, there can be generated a control signal to be used for controlling the number of rotations of the motor. Under this precondition, the stroke frequency can be adapted to the blood circulation rate required for the patient.

A preferred embodiment for realization of the closed triangular hypocycloidal path comprises an annular wheel in which a planet wheel with an outer toothing is rotatably held, said planet wheel having the coupling point for driving the piston eccentrically arranged thereon. This planet wheel is supported on a crank arm rotatably driven by the motor in continuous fashion, with the planet wheel running along the annular wheel having the inner toothing formed thereon, whose axis coincides with the rotational axis of the motor. The extent of eccentricity of the coupling point to the planet wheel determines the shape of the hypocycloidal path whereon the coupling point is moving. For obtaining a closed hypocycloidal path, the diameter of the annular wheel must be an integral multiple of the diameter of the planet wheel. For providing a hypocycloidal path of triangular shape, this ratio has to be 3:1. Then, the length of the stroke path is equal to the difference of the diameters of the annular wheel and the planet wheel. The employment of toothed wheels for generating the hypocycloidal paths is easily realized in construction. Friction and wear are low. In principle, the triangular hypocycloidal path can also be realized in some other manner, e.g. by means of a connecting link guide.

Preferably, the piston is connected to the coupling point by a rod, the support of the rod on both ends being provided by wear-resistant joints.

Since the piston itself is not guided along a specific path, the rod engaging the piston has to be provided with a guide means. For transforming the movement of the coupling point along the hypocycloidal path into a linear movement of the piston, there is provided a guide means for guiding the rod in such a manner that its piston-side end is moved exclusively in rectilinear direction. Preferably, this is accomplished by a guide bar arrangement which is supported on the housing and pivotably engages the rod, and which has its guide bars interconnected by wear-resistant joints. Selecting a construction consisting exclusively of pivoting joints offers the advantage of an increased service life as compared to a slot guidance. Further, a guide bar arrangement in its folded condition occupies little space in the guiding direction of the rod so that the piston can be retracted to a position close to the gear unit. Generally, also some other type of linear guidance can be used for the piston-side end of the rod.

If the instant apparatus is to be used as an artificial heart implant for independent operation, it is suitable to provide the pump housing with two chambers therein which replace the natural ventricles of the heart and each of which has a piston of its own; for each piston, there is provided an individual coupling point to be moved along a hypocycloidal path, the two hypocycloidal paths being arranged concentrically, but at a rotational displacement with respect to each other.

Suitably, the chambers and their pistons are arranged at opposite ends of the gear unit. If the arrangement of the pistons and the chambers within the pump housing is selected in such a manner that the stroke axes of the two pistons form an opening angle between about 120° and 170°, it is made possible to locate the ends of the chambers and thus their entrances and exits in close proximity to each other and therefore placing them in a favorable configuration with regard to the flow-line pattern and the anatomical conditions.

By way of alternative to simultaneous movement of the two pistons, it is suitable to operate both pistons substantially in opposite senses. In a gear unit having a planet wheel, this is advantageous in that a single planet wheel is sufficient for both pistons. Further, the load on the power source is uniform over time.

If both of the coupling points are eccentrically arranged on the same planet wheel, there is achieved a small-sized and light-weight construction without the piston rods intersecting each other, all of these features being of eminent importance for implants. In the case of the preferred arrangement of the two piston rods at equal distances from the center of the planet wheel, there are generated two hypocycloidal paths which are congruent, i.e. have equal size and shape, while being concentrically rotated against each other, with their concentrical rotational displacement depending on the mutual distance of the coupling points.

By adjustment of the annular wheel, the hypocycloidal paths can be rotated with respect to the stroke axis of the piston for thus influencing the course of the stroke. By rotational displacement of the annular wheel, the stationary period in the course of the stroke can be continuously shortened. This effect can be utilized for volume discharge control of the blood pump. For turning the annular wheel, an adjusting means, e.g. a self-locking worm gear can be provided.

BRIEF DESCRIPTION OF THE DRAWING

Embodiments of the will be described in greater detail hereunder with reference to the drawings.

FIG. 5 a schematic representation of the kinematics of another blood pump having a single piston and an adjustable annular wheel; and FIG. 6 a diagram illustrating the course of the strokes over time of the blood pump according to FIG. 5.

DESCRIPTION OF THE PREFERRED EMBODIMENTS

Figure 1:
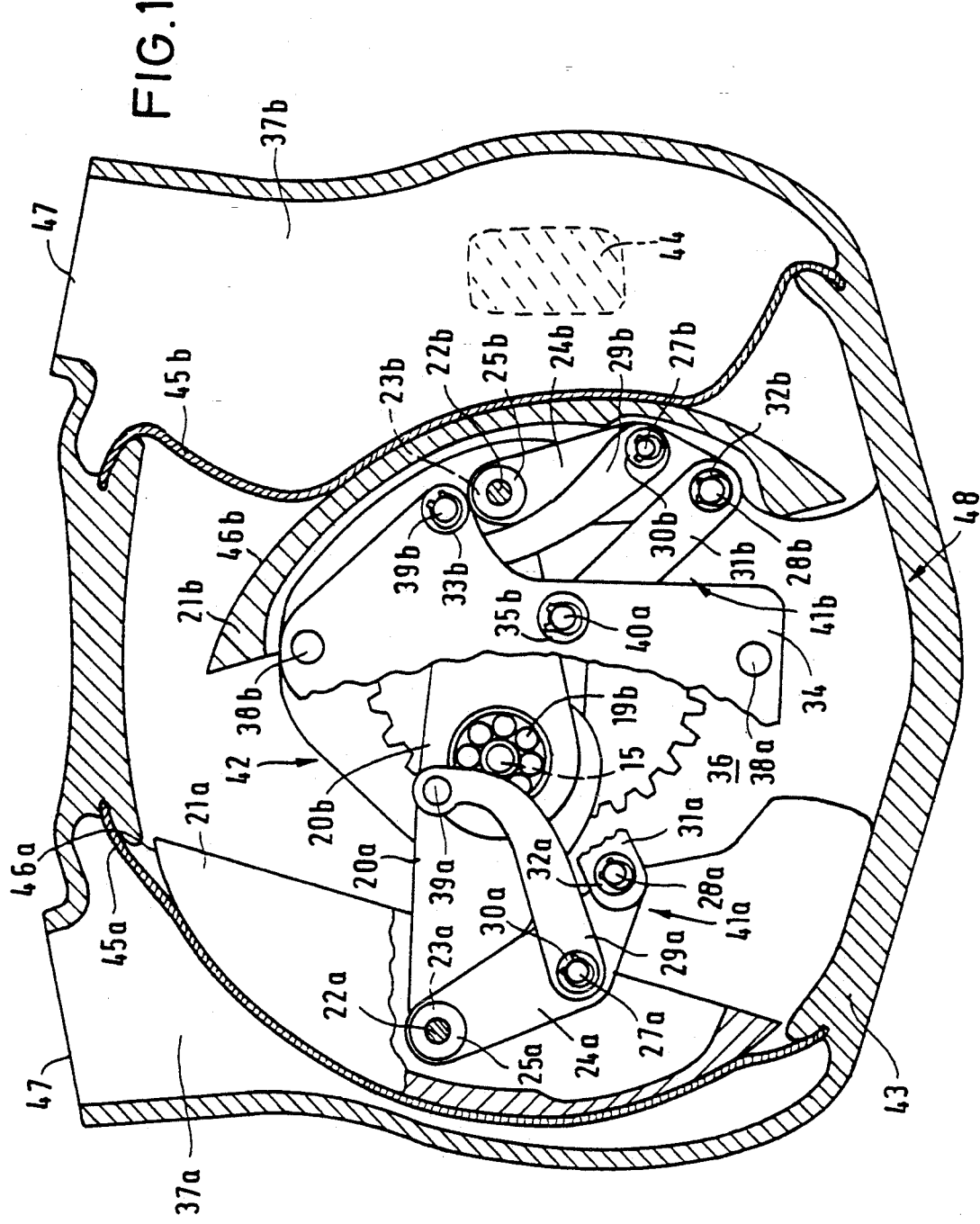
FIG. 1 is a sectional view of an embodiment of the blood pump of the invention, with some portions being omitted for reasons of clarity.

FIG. 1 is a sectional view of a blood pump for pulsating operation wherein some portions are omitted for illustrational purposes. A housing 43 accommodates two lateral blood chambers 37a and 37b provided with blood inlets 44 and blood outlets 47 shown in interrupted lines. The blood chambers 37a and 37b are limited in inward direction by membranes 45a and 45b, respectively.

Between said two chambers 37a and 37b, there is arranged an operating means 48 comprising a gear unit 42' two pistons 21a and 21b having capshape or eclipsoided faces 46a and 46b abutting the membranes 45a and 45b, and guide means 41a and 41b arranged to form a guide bar arrangement. During slow, automatic filling of the chambers 37a and 37b resp., the membrane 45a and 45b resp. will abut onto the outer face 46a and 46b resp., of the piston. Then, during continued filling of the chamber, the membrane 45a or 45b performs a rolling folding motion along the outer face of the piston without generating folds, overlaying portions or bruises in the membrane. As is apparent particularly from FIG. 2, each of the pistons 21a and 21b is connected to the gear unit 42 via a rod 20a and 20b resp. in such a manner that the center of gravity $S_a$ and $S_b$ of the piston $21_a$ and $21_b$ resp., is arranged substantially in the extension of this rod. Connection of the piston to the rod is effected by a joint 23a and 23b resp. The position of the center of gravity $S_a$ and $S_b$ resp. relative to the rods 20a and 20b resp. provides for a dynamic self-adjustment of the piston axes in the direction of the rods or the stroke axes $H_a$ and $H_b$ resp. extending normally to the piston face and shown in interrupted lines in FIG. 2, when the piston is retracted or put to a standstill. During its advance stroke, the piston is adjusted by the abutting membrane The gear unit 42 comprises an annular wheel 36 with an inner toothing, being fixed to housing 43, and a planet wheel 15 with an outer toothing, rotating uniformly within annular wheel 36. Planet wheel 15 is supported on a crank arm 14 which radially projects from a motor shaft 12 arranged coaxially to annular wheel 36. Rods 20a and 20b engage planet wheel 15 at a coupling point 19a and 19b resp. arranged; eccentrically to the axis 16 of planet wheel 15. The two coupling points 19a, 19b are located the same distance from the center of the planet wheel 15. Upon rotation of the planet wheel 15 within annular wheel 36, the coupling point 19a or 19b moves on a triangular closed hypocycloidal path $Z_a$ and $Z_b$ resp. The two coupling points 19a, 19b move on the respective hypocycloidal paths $Z_a$, $Z_b$ at a constant mutual distance which is smaller than a fifth of the inner circle diameter of the hypocycloidal paths $Z_a$, $Z_b$. The diameters of annular wheel 36 and planet wheel 15 are in an integral ratio to each other which in the present case is 3:1 so that the cycloidal path $Z_a$ and $Z_b$ resp. is closed, i.e. for safeguarding that, with each rotation of planet wheel 15, the same moving path is covered and thus the corner points of this path are always situated on the same positions. One of the corner points of $Z_a$ and $Z_b$ resp. is facing towards the associated piston 21a or 21b. This is effected in that, when the axis 16 of planet wheel 15 is located on the straight line passing through motor shaft 12 and joint 23a or 23b, also the coupling point 19a or 19b is located on this line, notably on the side of axis 16 facing away from motor shaft 12.

In case of predetermined diameters of annular wheel 36 and planet wheel 15, the extent of eccentricity of the coupling points 19a and 19b is decisive for the shape of the hypocycloidal paths $Z_a$ and $Z_b$. This extent of eccentricity is identical for both coupling points and in the instant case is selected such that this path has rounded edges and the sides of the path extend in a slightly convex manner.

Except for the hypocycloidal paths $Z_a$ and $Z_b$ which are rotationally displaced with respect to each other, the two constructional units comprising a piston 21a or 21b and a rod 20a or 20b are equal to each other. Those parts of the constructional units which correspond to each other are designated by identical reference numerals along with different reference letters "a" and "b", respectively.

In a case when the coupling point 19a and 19b, keeping equal distances from axis 16, are arranged opposite each other by 180°, the appertaining hypocycloidal paths are arranged at a rotational displacement of exactly 180° to each other. In this case, the stroke axes of the pistons would extend along a single straight line and the movements of the pistons would be performed exactly alternately. The outer faces of the pistons, oriented substantially vertically to the stroke axes, would be parallel, and, accordingly, this would be the case for the chambers as well. The mutual rotational displacement of the hypocycloidal paths depends on the positions of the coupling points at planet wheel 15 relative to each other The straight line passing through coupling point 19a and axis 16 of planet wheel 15 and the straight line passing through coupling point 19b and axis 16 define an opening angle $\beta$. The corners of the hypocycloidal path in turn define the position of the stroke axes $H_a$ and $H_b$ enclosing an opening angle $\alpha$. The opening angles $\alpha$ and $\beta$ are in the following relation to each other:

$$\beta = 3 \times (\alpha - 120°).$$

In the present embodiment, the stroke axes form an angle $\alpha < 180°$. Thus, the outlets 47 can be arranged closer to each other, which is desirable for anatomical reasons and because of the the flow characteristics.

The guide means 41a provides for the conversion of the path movement of the coupling point into a linear reversible stroke of piston 21a. Said guide means comprises three bars 24a,29a,31a which in combination form a guide bar arrangement.

The guide bars 29a and 31a have their first end supported on joints 33a and 35a fixedly arranged on the housing. Joint 35a is arranged in the vicinity of motor shaft axis 12. Joint 33a is arranged external of the circumference of annular wheel 36, with guide bar 29a crossing rod 20a. Guide bars 29a and 31a resp. can carry out circular pendulum movements around joints 33a and 35a resp. The second end of guide bar 31a is connected to a guide bar 24a by a joint 32a. The second end of guide bar 29a is connected to guide bar 24a by a joint 30a arranged at a intermediate location along the length of guide bar 24a. By means of a joint 25a, guide bar 24a has its other end connected to rod 20a, the axes of joints 23a and 25a coinciding with each other. Joint 25a is guided in such a manner by the guide bar arrangement 24a,29a,31a that, in the section of the moving path determined by the movement of coupling point 19a, it will perform a substantially linear movement in the direction of stroke axis $H_a$. The moving path $K_a$ of joint 25a obtained by the guide bar arrangement 24a,29a,31a is illustrated by interrupted lines. Of this movement path, however, only the rectilinear portion is used.

The configuration of the guide means 41b comprising a guide bar arrangement with guide bars 24b,29b,31b and guide bars 25b,30b,32b,33b,35b is provided in analogy to that of guide means 41a. When the piston is retracted, each of the guide bar arrangements is collapsed while projecting only to a small extent in the direction of the stroke axis. Thereby, the region between gear unit 42 and the retracted piston can be given small dimensions.

The operation of the embodiment will be described hereunder with reference to FIG. 2. The continuously driven motor shaft 12 moves the planet wheel 15, rotating about its 16, uniformly in clockwise direction along the inner wall of annular wheel 36. The coupling points 19a and 19b are displaced along the hypocycloidal paths $Z_a$ and $Z_b$ which are located in a vertical plane with respect to the motor shaft axis. The rods 20a and 20b, in dependence of the position of the appertaining coupling point, carry out movements which are imparted on the pistons 21a or 21b. The stroke length is identical with the difference between the diameters of annular wheel 36 and planet wheel 15. This difference corresponds to the length of the projection of the hypocycloidal path, e.g. $Z_a$, onto the associated stroke axis $H_a$. When the coupling point passes through the front corner of the hypocycloidal path facing toward the piston, the piston will occupy its maximum advance position. This applies to the position of piston 21a in FIG. 2. During continued rolling movement of planet wheel 15, the piston will be retracted until the coupling point reaches the next rearward corner of the hypocycloidal path. The traveling path from corner to corner of the hypocycloidal path corresponds to one revolution of planet wheel 15. The portion of the hypocycloidal path averted from piston 21a, extending nearly at a right angle to the stroke axis, has a curvature substantially similar to that of a circle whose radius corresponds to the length of rod 20a between coupling point 19a and joint 23a. Thus, the movement of the piston in this part of the path is extremely small while coupling point 19a passes through this arc segment.

Figure 2:
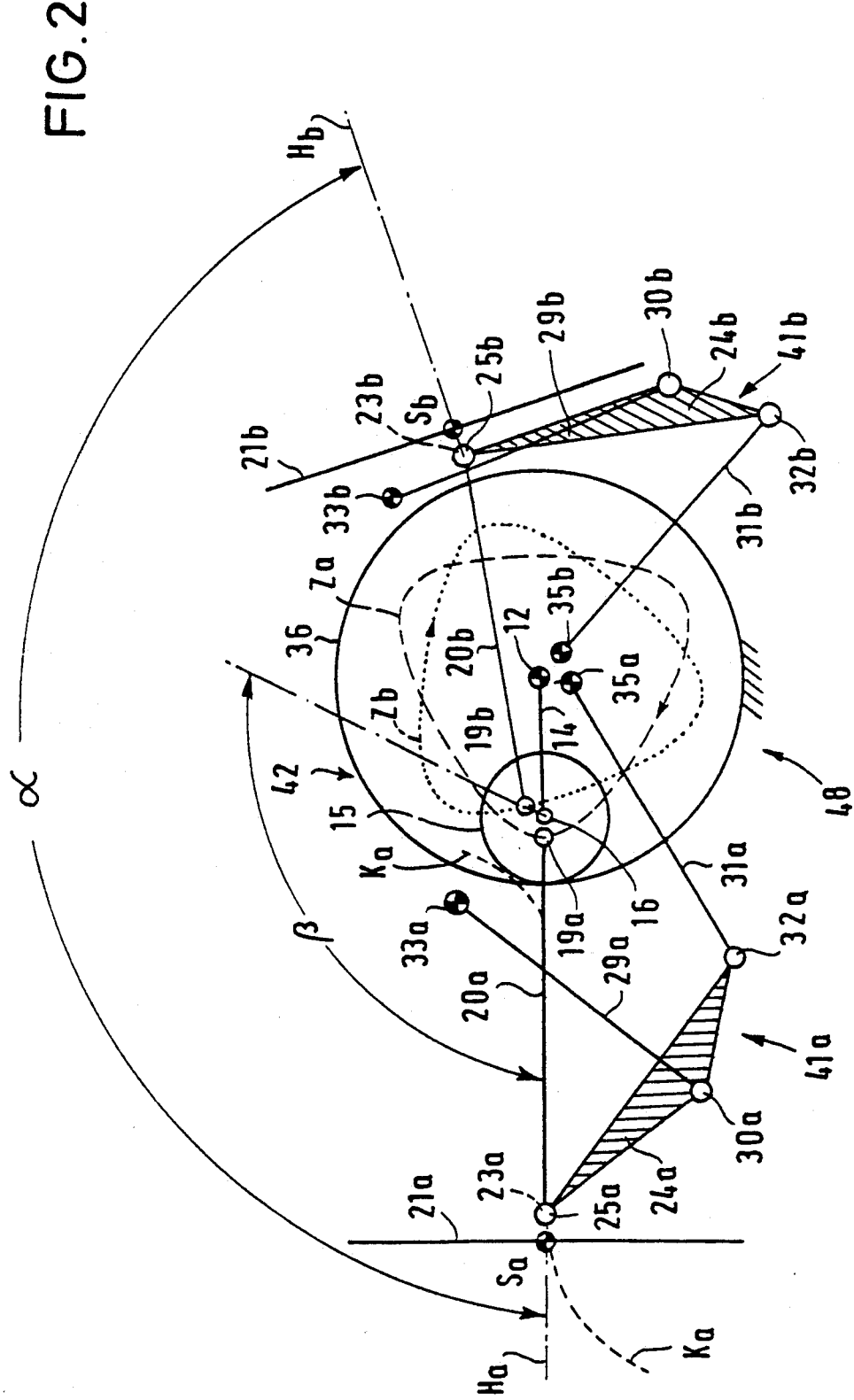
FIG. 2 a schematic representation of the kinematics of the blood pump.

In FIG. 2, the coupling point 19b of rod 20b is located on the rearward portion of the hypocycloidal path $Z_b$.

When passing the third corner, the piston resumes an advance movement and reaches its maximum advance position after completion of the third revolution of planet wheel 15.

Due to the guide bar arrangement 24a,29a,31a and 24b, 29b,31b resp., the end of rod 20a or 20b arranged outside annular wheel 36 and the piston 21a or 21b connected to said rod can merely perform a movement in the direction of stroke axis $H_a$ or $H_b$. Therefore, the guide bar arrangement carries the weight of the piston and the rod. In accordance with the advance position of the piston, the guide bar arrangement will move into its folded or extended state.

Next, the course of the stroke movements over time will be explained in connection with the diagram of FIG. 3 wherein the abscissa indicates the time t and the ordinate indicates the piston stroke h. The pumping cycle extends from the time $t_0$ up to T. During the pumping cycle, the planet wheel 15 carries out three revolutions and the crank arm 14 carries out one full revolution. The value $h_{max}$ is the amount of the maximum advance position of a piston whose minimum advance position is given at h=0.

Figure 3:
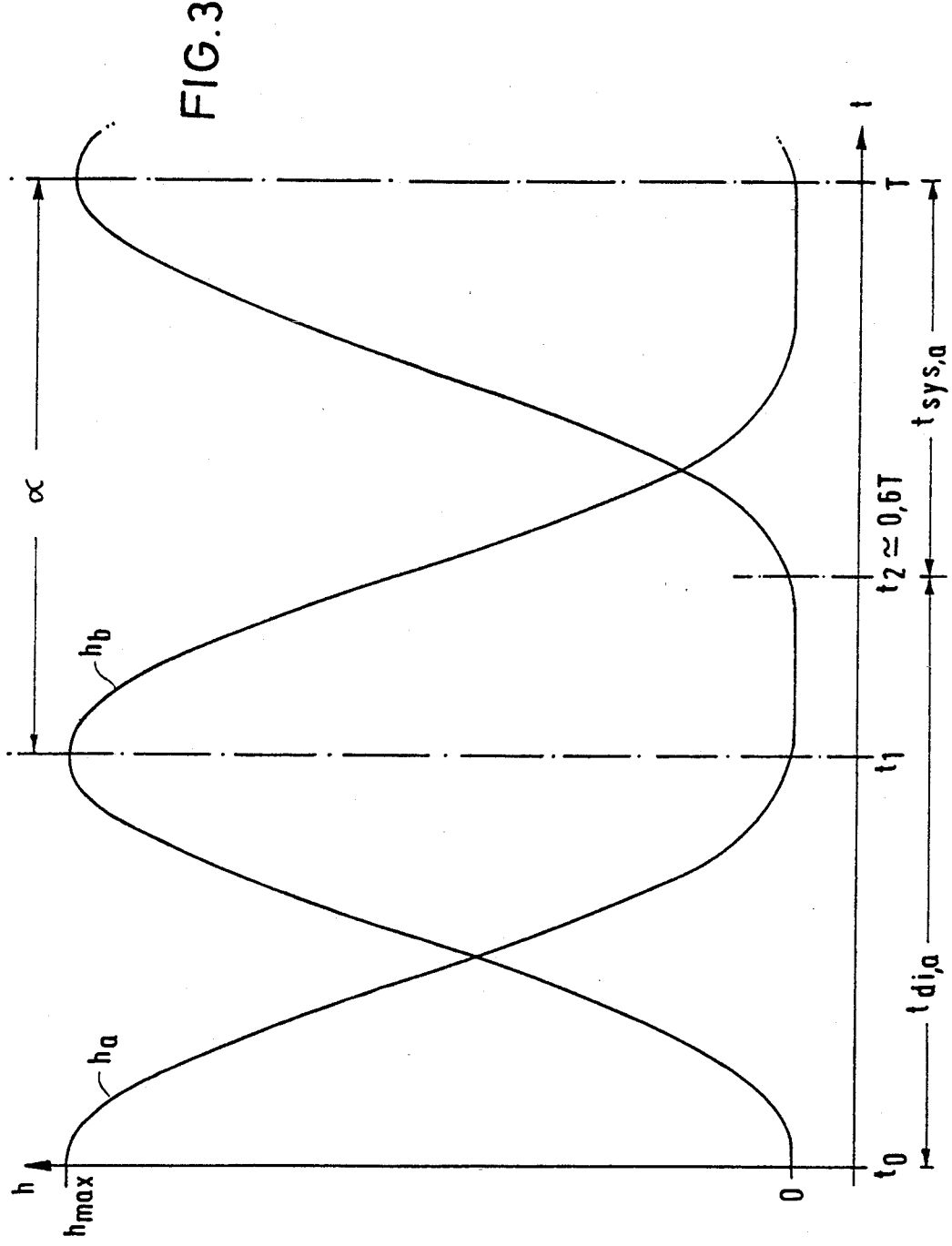
FIG. 3 a diagram illustrating the course of the strokes over time of the blood pump.

The positions $h_a$ and $h_b$ of the piston at the time $t_0$ and the time T according to FIG. 3 correspond to the positions of the piston 21a and 21b shown in FIG. 2. With continued movement, piston 21a performs a return stroke period which lasts up to about $t_1=0.4T$ and at this point reaches the minimum value $h_a=0$. During the period of a stationary stroke until about $t_2=0.6T$, $h_a$ will be kept at the value zero. In a subsequent advance stroke period, piston 21 again reaches it maximum value $h_a=h_{max}$. Accordingly, the length $t_{sysa}$ of the systole amounts to about 40% of the cycle time while the length $T_{dia}$ of the diastole amounts to about 60% of the cycle time. The same movement is also performed by piston 21b, but with a shifting in phase by about 150°.

The phase angle between the two courses $h_a(t)$ and $h_b(t)$ is identical with the opening angle $\alpha$ of the stroke axes.

Figure 4:
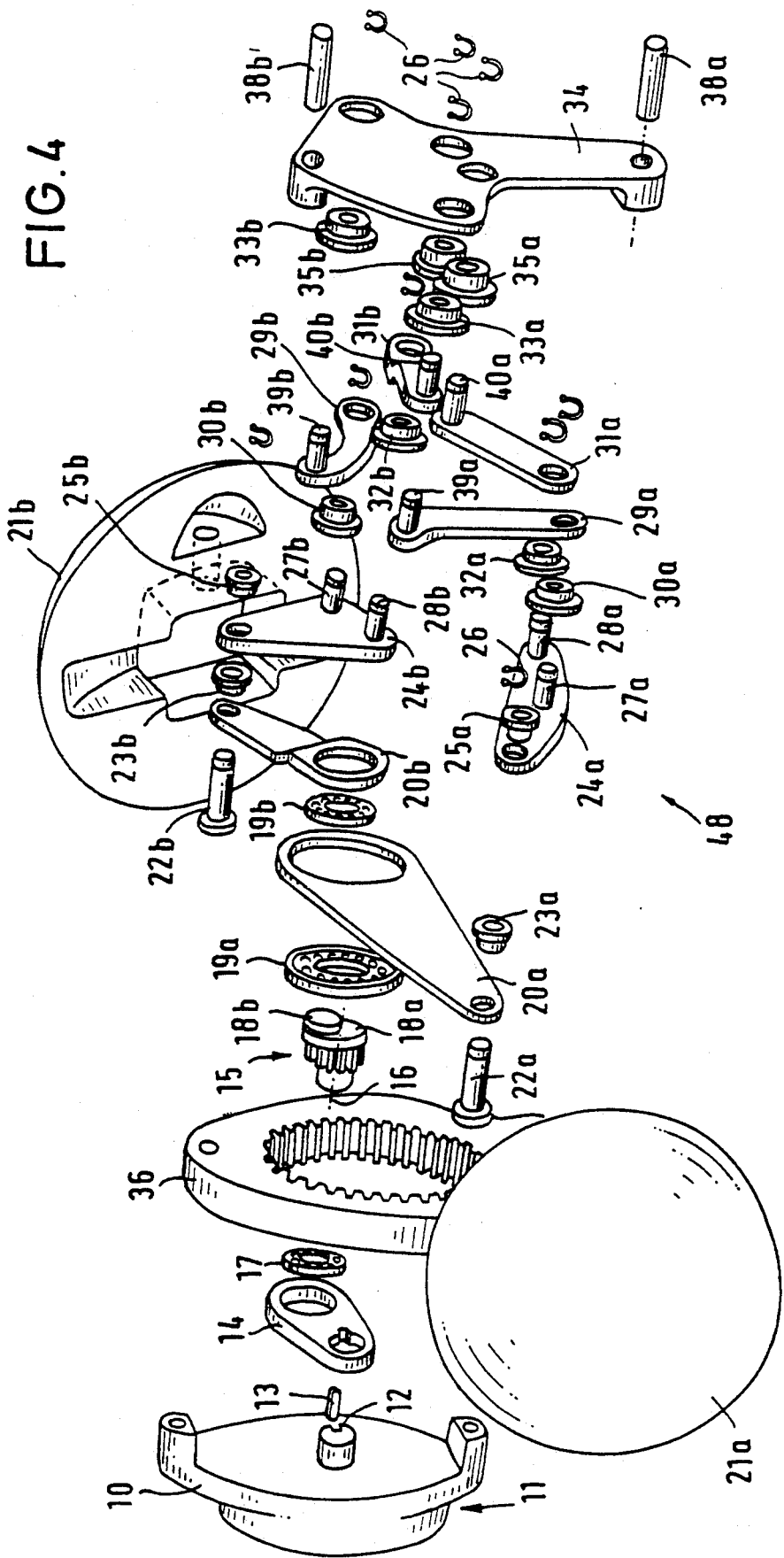
FIG. 4 a diametric exploded view of the blood pump.

The constructional arrangement of the blood pump of FIGS. 1 and 2 will be explained hereunder with reference to the exploded view of FIG. 4.

A rotating shaft 12 projects out from the housing 10 of a motor 11. Through use of an adjusting spring 13, the crank arm 14 is fastened to shaft 12. The other end of crank arm 14 is connected to planet wheel 15 by a pivot bearing 17. On the side of planet wheel 15 facing away from crank arm 14, there are arranged two shaft butts 18a and 18b having their centers displaced with respect to axis 16 of planet wheel 15. The coupling points 19a and 19b are formed by pivot bearings provided on one end of rods 20a and 20b and supporting the shaft butts 18a and 18b.

On the other end of rod 20a, piston 21a is supported by means of a pin 22a and the pivot joint 23a. Also at pin 22a, guide bar 24a is supported by pivot joint 25a. Guide bar 24a is provided with two laterally projecting cylindrical pivots 27a and 28a. On pivot 27a, guide bar 29a is supported by pivot joint 30a. On pivot 28a, guide bar 31a is supported by pivot joint 32a. Guide bars 29a or 31a have their ends remote from guide bar 24a provided with respective lateral cylindrical pivots 39a and 40a resp. By pivot 39a and pivot joint 33a, guide bar 29a is supported in a holding plate 34. Guide bar 31a is connected to holding plate 34 through pivot joint 35a.

In analogue configuration thereto, rod 20b, piston 21b, pin 22b, guide bars 24b, 29b, 31b are connected to the respective pivots 27b, 28b, 39b and 40b as well as to pivot joints 23b, 25b, 30b, 32b, 33b and 35b and to holding plate 34. All of the pivot joints are secured against axial displacement by clamping rings 26.

FIG. 5 shows a blood pump comprising a single piston 21a and an adjustable annular wheel 36'. Construction and operation of gear unit 42, guide means 41a, piston 21a are otherwise the same as in the embodiment according to FIGS. 1-4.

The outer circumference of annular wheel 36' has a toothing segment 49 formed thereon which together with a worm shaft 50 constitutes a self-locking worm gear. Upon rotation of worm shaft 50, annular wheel 36' is rotated about its axis by the angle y which is formed between the stroke axis $H_a$ and the front corner of the hypocycloidal path $Z_a$.

This rotating movement causes a change of the course h(t) of the stroke of piston 21a. In FIG. 6, the courses of the strokes $h_a(t)$ at y=0° and $h_a(t)$ at y=30° are indicated in a diagram similar to FIG. 3. The course of the stroke $h_a(t)$ at y=0° corresponds to the one shown in FIG. 3. The course of the stroke $h_a(t)$ at y=30° has a maximum value being slightly smaller than $h_{max}$ and a minimum value which being also smaller than at y=0. The maximum values are shifted with respect to each other by a period angle which substantially corresponds to the angle y. Here, the return and advance stroke periods will last about 0.5T, whereas the stationary stroke period is omitted. The above described blood pump is particularly suited for an artificial heart implant. However, it is also useful for extracorporeal applications.

We claim:

1. A blood pump for pulsating operation, comprising at least one chamber (37a, 37b) arranged in a pump housing (43) and an operating means (48) driven by a continuously rotating motor (11), said operating means (48) including at least one piston (21a, 21b) for periodically changing the chamber volume and gear unit means (42) for moving a coupling point along a closed moving path (19a, 19b), with the coupling point connecting to the at least one piston (21a, 21b) for driving the at least one piston (21a, 21b), characterized in that the coupling point closed moving path is a triangular hypocycloidal path ($Z^a$, $Z^b$) having one of its corners facing towards the at least one piston (21a, 21b).

2. The blood pump according to claim 1, characterized in that the hypocycloidal path ($Z_a$,$Z_b$) is arranged in such a manner that, in a piston cycle, the at least one piston (21a,21b) performs an advance stroke period, a return stroke period and a stationary stroke period, the advance stroke period occupying about 40% of the cycle time.

3. The blood pump according to claim 1, characterized in that the operating means comprises a planet wheel (15) having an outer toothing and moving along an annular wheel (36) having an inner toothing, the coupling point (19a,19b) being arranged eccentrically on the planet wheel (15).

4. The blood pump according to claim 3, characterized in that the rotational position of the annular wheel (36) is variable.

5. The blood pump according to claim 3, characterized in that the planet wheel 15, is supported on a crank arm (14) rotatingly driven in continuous fashion by the motor (11), the rotational axis of the motor (11) coinciding with the axis of the annular wheel (36).

6. The blood pump according to claim 1, characterized in that the coupling point (19a, 19b) rotatably supports a rod (20a,20b) having its other end connected to the piston (21a,21b) through a pivot joint (23a,23b).

7. The blood pump according to claim 6, characterized in that a guide means (41a) is provided for guiding the piston-side end of the rod (20a,20b) along a rectilinear path.

8. The blood pump according to claim 7, characterized in that the guide means comprises a guide bar arrangement (24a,29a,31a;24b,29b,31b) fixedly supported on the pump housing (43) and pivotably engaging the rod (20a,20b).

9. The blood pump according to claim 6 characterized in that the center of gravity (5a,5b) of the piston (21a,21b) is located in extension of the rod (20a,20b).

10. The blood pump according to claim 1, characterized in that the pump housing (43) comprises two chambers (37a,37b) with one piston (21a,21b) respectively, each of the pistons (21a, 21b) having assigned thereto an individual coupling point (19a,19b) moving along a respective hypocycloidal path ($Z_a, Z_b$), with the hypocycloidal paths ($Z_a, Z_b$) being arranged concentrically but at a rotational displacement from each other.

11. The blood pump according to claim 10, characterized in that the two coupling points (19a,19b) move on the respective hypocycloidal paths ($Z_a, Z_b$) at a constant mutual distance which is smaller than a fifth of the inner circle diameter of the hypocycloidal paths ($Z_a, Z_b$).

12. The blood pump according to claim 10, characterized in that the stroke axes of the two pistons (21a, 21b) define an opening angle ($\alpha$) between 120° and 170°.

13. The blood pump according to claim 10, characterized in that the change of volume in the chambers (37a,37b) of the pump housing (43) is performed alternately.

14. The blood pump according to claim 10, characterized in that the operating means comprises a planet wheel (15) having an outer toothing and moving along an annular wheel (36) having an inner toothing, both of the coupling points (19a, 19b) being arranged eccentrically on the planet wheel (15).

15. The blood pump according to claim 14, characterized in that the two coupling points (19a,19b) are located at the same distance from the center of the planet wheel (15).

16. The blood pump according to claim 1, characterized in that the piston; (21a,21b) has an ellipsoidal outer face (46a,46b).

* * * * *